United States Patent [19]

Pastor et al.

[11] Patent Number: 5,414,028
[45] Date of Patent: May 9, 1995

[54] CARBOHYDRATE SUBSTITUTED DIBENZO[D,F][1,3,2]DIOXAPHOSPHEPIN STABILIZERS

[75] Inventors: Stephen D. Pastor, Danbury, Conn.; Joseph E. Babiarz, Amawalk, N.Y.

[73] Assignee: Ciba-Geigy Corporation, Ardsley, N.Y.

[21] Appl. No.: 198,017

[22] Filed: Feb. 17, 1994

Related U.S. Application Data

[62] Division of Ser. No. 918,324, Jul. 22, 1992, Pat. No. 5,310,889.

[51] Int. Cl.$^6$ .................. C08K 5/52; C08L 23/12; C09K 15/32
[52] U.S. Cl. .................. 524/30; 252/400.24; 524/27; 524/29; 524/32; 524/33; 524/117; 524/118; 524/119; 524/514; 524/583; 524/606; 558/4; 558/147; 558/78; 536/4.1; 536/17.1; 987/40; 987/41
[58] Field of Search .................. 536/17.1, 4.1; 524/27, 524/30, 29, 583, 606, 32, 33, 117, 118, 119, 514; 252/400.24; 987/40, 41; 554/4; 558/147, 78

[56] References Cited

U.S. PATENT DOCUMENTS

| | | |
|---|---|---|
| 4,143,028 | 3/1979 | Spivack . |
| 4,196,117 | 4/1980 | Spivack . |
| 4,252,750 | 2/1981 | Buysch et al. . |
| 4,259,492 | 3/1981 | Rasberger . |
| 4,318,845 | 3/1982 | Spivack et al. . |
| 4,374,219 | 2/1983 | Spivack et al. . |
| 4,381,359 | 4/1983 | Idel et al. . |
| 4,524,166 | 6/1985 | Spivack et al. . |
| 4,551,495 | 11/1985 | Brassat et al. . |
| 4,599,206 | 7/1986 | Billig et al. . |
| 4,737,588 | 4/1988 | Billig et al. . |
| 4,764,605 | 8/1988 | Hanessian et al. . |
| 4,835,299 | 5/1989 | Maher et al. . |
| 5,292,785 | 3/1994 | Pastor et al. .......... 524/117 |
| 5,310,889 | 5/1994 | Pastor et al. .......... 536/17.1 |

OTHER PUBLICATIONS

Sulfur Letters vol. 9 (1–2) pp. 39–45.

*Primary Examiner*—Herbert J. Lilling
*Attorney, Agent, or Firm*—Luther A. R. Hall

[57] ABSTRACT

Carbohydrate substituted dibenzo[d,f][1,3,2]dioxaphosphepin compounds of formula I

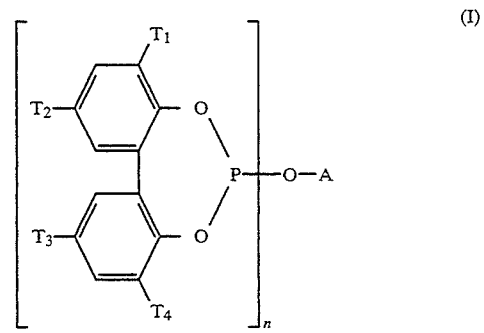

where A is a carbohydrate residue are effective stabilizers for polymers processed at elevated temperatures and subject to thermal or oxidative degradation.

11 Claims, No Drawings

CARBOHYDRATE SUBSTITUTED DIBENZO[D,F][1,3,2]DIOXAPHOSPHEPIN STABILIZERS

This is a divisional of application Ser. No. 07/918,324, filed on Jul. 22, 1992, now U.S. Pat. No. 5,310,889, issued on May 10, 1994.

The instant invention pertains to carbohydrate substituted dibenzo[d,f][1,3,2]dioxaphosphepins and polymer compositions stabilized against thermal and oxidative degradation containing said phosphites.

BACKGROUND OF THE INVENTION

Phosphites have long been used as stabilizers for organic materials subject to oxidative or thermal degradation. Particularly valuable for this purpose are the substituted aryl phosphites.

Substituted dibenzo[d,f][1,3,2]dioxaphosphepins are described in U.S. Pat. Nos. 4,143,028; 4,259,492; 4,318,845; 4,374,219; 4,524,166; 4,599,206; 4,737,588 and 4,835,299, but none of the compounds described contain a carbohydrate moiety.

A carbohydrate derivative of dibenzo[d,g][1.3.6.2]dioxathiaphosphocin is described in Sulfur Letters, 9,39 (1989) as a ligand for the gold catalyzed reaction of benzaldehyde and methyl α-isocyanatoacetate to prepare oxazolines.

The instant carbohydrate compounds are new as are the stabilized compositions containing said compounds.

OBJECTS OF THE INVENTION

One object of this invention is to provide new carbohydrate derivatives of dibenzo[d,f][1,3,2]dioxaphosphepin.

Another object of the invention is to provide stabilized compositions of an organic material subject to thermal or oxidative degradation stabilized against said degradation by an effective stabilizing amount of a new carbohydrate derivative of dibenzo[d,f][1,3,2]dioxaphosphepin.

DETAILED DISCLOSURE

The instant invention pertains to a compound of formula I

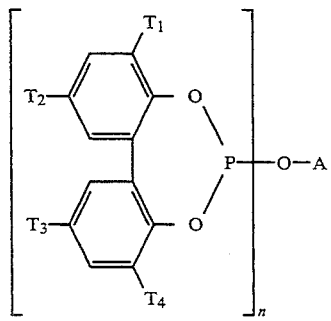

wherein
n is 1 to 6,
$T_1$, $T_2$, $T_3$ and $T_4$ are independently alkyl of 1 to 12 carbon atoms, cycloalkyl of 5 to 12 carbon atoms, aryl of 6 to 10 carbon atoms or phenylalkyl of 7 to 15 carbon atoms, and
A is a carbohydrate residue which is a radical, diminished by a hydroxyl or thiol group or an amine hydrogen atom, of a protected monohydroxy-functional, monothiol-functional or monoamine-functional sugar, thio-sugar or amino-sugar or derivatives thereof belonging to the group of sugar alcohols, esters of sugar acid, aldo-sugar acid or keto-sugar acid, amino-sugar, sugar mercaptal or deoxy-sugar.

Preferably, n is 1 to 3 and most preferably 1.

Preferably, $T_1$ and $T_4$ are independently alkyl of 3 to 8 carbon atoms or phenylalkyl of 7 to 9 carbon atoms.

Preferably, $T_2$ and $T_3$ are independently alkyl of 1 to 8 carbon atoms, cyclohexyl, phenyl or phenylalkyl of 7 to 9 carbon atoms.

Most preferably, $T_1$ to $T_4$ are independently alkyl of 4 to 8 carbon atoms; and especially each of $T_1$ to $T_4$ is tert-butyl.

A is preferably the radical of a protected monohydroxy-functional, monothiol-functional or monoamino-functional $C_3$–$C_7$-monosaccharide or corresponding disaccharides or trisaccharides or derivatives thereof belonging to the group of the sugar alcohols, esters of a sugar acid, aldo-sugar acid or keto-sugar acid, amino-sugars, deoxysugars or sugar-mercaptals.

A is particularly preferably the radical of a $C_3$–$C_7$-monosaccharide, especially a $C_5$ or $C_6$ monosaccharide, or derivatives thereof. In particular, A is the radical of a furanose or pyranose.

The sugars from which A is derived can be, for example, aldoses or ketoses. Examples are: glyceraldehyde, erythrose, threose, arabinose, ribose, xylose, lyxose, glucose, mannose, allose, galactose, fructose, gulose, altrose, idose, talose, ribulose, erythrulose, xylulose, psicose, sorbose and tagatose. The sugars can be in an open-chain or cyclized form, for example in the form of furanoses or pyranoses.

Examples of disaccharides and trisaccharides are sucrose, maltose, lactose, raffinose, maltotriose and cellobiose.

Examples of sugar alcohols from which A can be derived are sorbitol and mannitol.

The sugar acids, aldo-sugar acids and keto-sugar acids from which A can be derived can be in the form of lactones or esters, the ester group or ester groups preferably containing $C_1$–$C_4$-alkyl, in particular methyl. Examples of such acids are gluconic acid, saccharic acid, mannosaccharic acid, mannonic acid and uronic acids, for example glucuronic acid and also neuraminic acid and ascorbic acid.

Glucosamine, galactosamine and mannosamine are typical examples of amino-sugars from which A can be derived.

Glucose dimethyl mercaptal and thioglucoside are typical sugar mercaptals from which A can be derived.

2-Deoxyribofuranose, rhamnose, fucose and digitoxose are examples of deoxy-sugars from which A can be derived.

More particularly, A in the compound of formula I is a suitably protected monosaccharide of Formula II or III

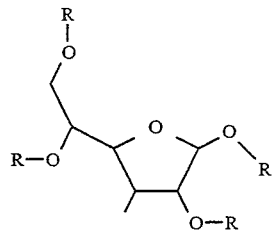

-continued

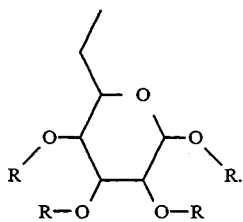

III where R is a suitable protecting group which is benzyl or acetyl, or two vicinal R groups are isopropylidene; preferably the protecting group is isopropylidene.

When n is 2 to 6, one or more of the protecting groups R is absent from formula II or III allowing for the group A to be polyvalent.

The instant invention also pertains to a stabilized composition which comprises (a) an organic material subject to oxidative or thermal degradation, and (b) an effective stabilizing amount of a compound of formula I

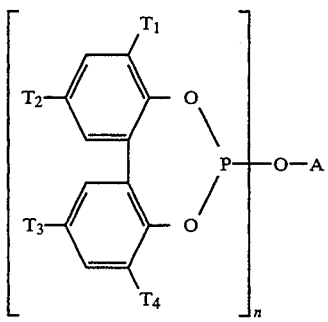

(I)

wherein n is 1 to 6, $T_1$, $T_2$, $T_3$ and $T_4$ are independently alkyl of 1 to 12 carbon atoms, cycloalkyl of 5 to 12 carbon atoms, aryl of 6 to 10 carbon atoms or phenylalkyl of 7 to 15 carbon atoms, and A is a carbohydrate residue which is a radical, diminished by a hydroxyl or thiol group or an amine hydrogen atom, of a protected monohydroxy-functional, monothiol-functional or monoamine-functional sugar, thio-sugar or amino-sugar or derivatives thereof belonging to the group of sugar alcohols, esters of sugar acid, aldo-sugar acid or keto-sugar acid, amino-sugar, sugar mercaptal or deoxy-sugar.

The organic material is preferably a polymer processed at elevated temperatures. Particularly preferred organic polymers are the polyolefins, especially polypropylene and polyethylene, and polyamides. Most particularly the organic polymer is polypropylene.

When any of $T_1$ to $T_4$ is alkyl, such alkyl groups are, for example, methyl, ethyl, isopropyl, n-butyl, isobutyl, tert-butyl, tert-amyl, 2-ethylhexyl, n-octyl, tert-octyl, lauryl and tert-dodecyl; when such radicals are cycloalkyl, they are, for example, cyclopentyl, cyclohexyl, cyclooctyl and cyclododecyl; when said radicals are phenylalkyl, they are, for example benzyl, phenethyl, α-methylbenzyl and α,α-dimethylbenzyl; when said radicals are aryl, they are, for example, phenyl, tolyl, xylyl and naphthyl.

The carbohydrate moieties A are selected from the group consisting of sugars described above.

The compounds of this invention are conveniently prepared by the reaction of the carbohydrate containing appropriate protecting groups with the corresponding chloro intermediate of dibenzo[d,f][1,3,2]dioxaphosphepin which is prepared by the reaction of phosphorus trichloride and the appropriate bisphenol in the presence of an amine acid acceptor such as triethylamine.

The compounds of this invention are very effective processing stabilizers for polyolefins than the prior art compounds both in preventing molecular weight changes as well as preventing discoloration.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from α,β-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
   1.1. Alkylated monophenols, for example,
   2,6-di-tert-butyl-4-methylphenol
   2-tert-butyl-4,6-dimethylphenol
   2,6-di-tert-butyl-4-ethylphenol
   2,6-di-tert-butyl-4-n-butylphenol
   2,6-di-tert-butyl-4-i-butylphenol
   2,6-di-cyclopentyl-4-methylphenol
   2-(α-methylcyclohexyl)-4,6-dimethylphenol
   2,6-di-octadecyl-4-methylphenol
   2,4,6-tri-cyclohexylphenol
   2,6-di-tert-butyl-4-methoxymethylphenol
   1.2. Alkylated hydroquinones, for example,
   2,6-di-tert-butyl-4-methoxyphenol
   2,5-di-tert-butyl-hydroquinone
   2,5-di-tert-amyl-hydroquinone
   2,6-diphenyl-4-octadecyloxyphenol
   1.3. Hydroxylated thiodiphenyl ethers, for example,
   2,2'-thio-bis-(6-tert-butyl-4-methylphenol)
   2,2'-thio-bis-(4-octylphenol)
   4,4'-thio-bis-(6-tert-butyl-3-methylphenol)
   4,4'-thio-bis-(6-tert-butyl-2-methylphenol)
   1.4. Alkylidene-bisphenols, for example,
   2,2'-methylene-bis-(6-tert-butyl-4-methylphenol)
   2,2'-methylene-bis-(6-tert-butyl-4-ethylphenol)
   2,2'-methylene-bis-[4-methyl-6-(α-methylcyclohexyl)-phenol]
   2,2'-methylene-bis-(4-methyl-6-cyclohexylphenol)
   2,2'-methylene-bis-(6-nonyl-4-methylphenol)
   2,2'-methylene-bis-[6-(α-methylbenzyl)-4-nonylphenol]
   2,2'-methylene-bis-[6-(α,α-dimethylbenzyl)-4-nonylphenol]
   2,2'-methylene-bis-(4,6-di-tert-butylphenol)
   2,2'-ethylidene-bis-(4,6-di-tert-butylphenol)
   2,2'-ethylidene-bis-(6-tert-butyl-4-isobutylphenol)
   4,4'-methylene-bis-(2,6-di-tert-butylphenol)
   4,4'-methylene-bis-(6-tert-butyl-2-methylphenol)
   1,1-bis-(5-tert-butyl-4-hydroxy-2-methylphenyl)-butane
   2,6-di-(3-tert-butyl-5-methyl-2-hydroxybenzyl)-4-methylphenol
   1,1,3-tris-(5-tert-butyl-4-hydroxy-2-methylphenyl)-butane
   1,1-bis-(5-tert-butyl-4-hydroxy-2-methylphenyl)-3-n-dodecylmercaptobutane
   ethyleneglycol bis-[3,3-bis-(3'-tert-butyl-4'-hydroxyphenyl)-butyrate]
   di-(3-tert-butyl-4-hydroxy-5-methylphenyl)-dicyclopentadiene
   di-[2-(3'-tert-butyl-2'-hydroxy-5'-methyl-benzyl)-6-ten-butyl-4-methylphenyl]terephthalate.
   1.5. Benzyl compounds, for example,
   1,3,5-tri-(3,5-di-tert-butyl-4-hydroxybenzyl)-2,4,6-trimethylbenzene
   di-(3,5-di-tert-butyl-4-hydroxybenzyl) sulfide
   3,5-di-ten-butyl-4-hydroxybenzyl-mercapto-acetic acid isooctyl ester
   bis-(4-tert-butyl-3-hydroxy-2,6-dimethylbenzyl)dithiol terephthalate
   1,3,5-tris-(3,5-di-tert-butyl-4-hydroxybenzyl) isocyanurate
   1,3,5-tris-(4-tert-butyl-3-hydroxy-2,6-dimethylbenzyl) isocyanurate
   3,5-di-tert-butyl-4-hydroxybenzyl-phosphoric acid dioctadecyl ester
   3,5-di-tert-butyl-4-hydroxybenzyl-phosphoric acid monoethyl ester, calcium-salt
   1.6. Acylaminophenols, for example,
   4-hydroxy-lauric acid anilide
   4-hydroxy-stearic acid anilide
   2,4-bis-octylmercapto-6-(3,5-tert-butyl-4-hydroxyanilino)-s-triazine
   octyl-N-(3,5-di-tert-butyl-4-hydroxyphenyl)-carbamate
   1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
   N,N'-di-(3,5-di-tert-butyl-4-hydroxyphenylpropionyl)-hexamethylenediamine
   N,N'-di-(3,5-di-tert-butyl-4-hydroxyphenylpropionyl)-trimethylenediamine
   N,N'-di-(3,5-di-tert-butyl-4-hydroxyphenylpropionyl)-hydrazine
   1.10 Diarylamines, for example,
   diphenylamine, N-phenyl-1-naphthylamine, N-(4-tert-octylphenyl)-1-naphthylamine,
   4,4'-di-tert-octyl-diphenylamine, reaction product of N-phenylbenzylamine and
   2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers
   2.1. 2-(2'-hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-,5-chloro-3'-tert-butyl-5'-methyl-, 3'-sec-butyl-5'-tert-butyl-, 4'-octoxy, 3',5'-di-tert-amyl-,3',5'-bis(α,α-dimethylbenzyl), 3'tert-butyl-5'-(2-(omega-hydroxy-octa-(ethyleneoxy)carbonyl-ethyl)-,3'-dodecyl-5'-methyl-, and 3'-tert-butyl-5'-(2-octyloxycarbonyl)ethyl-, and dodecylated-5'-methyl derivatives.
   2.2. 2-Hydroxy-benzophenones, for example, the 4-hydroxy-, 4-methoxy-, 4-octoxy, 4-decyloxy-,4-dodecyloxy-, 4-benzyloxy, 4,2',4'-trihydroxy- and 2'-hydroxy-4,4'-dimethoxy derivatives.
   2.3. Esters of optionally substituted benzoic acids for example, phenyl salicylate, 4-tert-butylphenyl salicylate, octylphenyl salicylate, dibenzoylresorcinol, bis-(4- tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpipefidyl) sebacate, bis-(1,2,2,6,6-pentamethylpiperidyl) sebacate, n-butyl-3,5-di-tert-butyl-4-hydroxybenzyl malonic acid bis-(1,2,2,6,6-pentanemethylpiperidyl)ester, condensation product of 1-hydroxyethyl-2,2,6,6tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpipefidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethyl-piperazinone), bis(1-octyloxy-2,2,6,6-tetramethylpiperidin-4-yl) sebacate.

2.7. Oxalic acid diamides, for example, 4,4'-dioctyloxy-oxanilide, 2,2'-di-octyloxy-5,5'-di-tert-butyl-oxanilide,2,2'-di-dodecyloxy-5,5'-di-tert-butyl-oxanilide, 2-ethoxy-2'-ethyloxanilide and its N,N'-bis (3-dimethylaminopropyl)-oxalamide, 2-ethoxy-5-tert-butyl-2'-ethyl-oxanilide, mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alphaheptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tertbutyl-4-hydroxyhydrocinnammate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylene-bis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis( 1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β',-tetramethyl-3,9-(2,4,8,10-tetraoxaspiro[5.5]-undecane)diethyl]1,2,3,4-butanetetracarboxylate, mixed [1,2,2,6,6-pentamethylpiperidin-4-yl/β,β, β', β'-tetramethyl-3,9-(2,4,8,10-tetraoxspiro[5.5]-undecane)diethyl]1,2,3,4-butanetetracarboxylate, octamethylene bis(2,2,6,6-tetramethylpiperdin-4-carboxylate), 4,4'-ethylenebis(2,2,6,6-tetramethylpiperazin-3-one), and bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent bright-stocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: $G_1$—OCC-alkylene-COO$G_2$ wherein "alkylene" denotes an alkylene residue having from 2 to 14 carbon atoms and $G_1$ and $G_2$ are the same or different and each is an alkyl group having from 6 to 18 carbon atoms. Tri-esters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rest inhibitors, extreme pressure additives, anti-wear additives and antioxidants.

Examples of Phenolic Antioxidants

1. Alkylated Monophenols 2,6-Di-tert-butyl-4-methylphenol, 2,6-di-tert-butylphenol, 2-tert-butyl-4,6-dimethylphenol,2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)4,6-dimethylphenol, 2,6-di-octa-decyl-4-methylphenol, 2,4,6-tri-cyclohexylphenol, 2,6-di-tert-butyl-4-methoxymethylphenol, o-tert-butylphenol.
2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.
3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).
4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5- isobutylphenol), 2,2′-methylene-bis-(6-(α-methylbenzyl-4-nonylphenol), 2,2′-methylene-bis-(6-(α,α-dimethylbenzyl)-4-nonylphenol), 4,4′-methylene-bis-(2,6-di-tert-butyl-phenol), 4,4′-methylene-bis-(6-tert-butyl-2-methylphenol), 1,1-bis-(5-tert-butyl-4-hydroxy-2methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methylphenyl)-3-n-dodecyl)-mercaptobutane, ethyleneglycol-bis-[3,3-bis-(3′-tert-butyl-4′-hydroxyphenyl)-butyrate], bis-(3-tert-butyl-4-hydroxy-5-methylphenyl)-dicyclopentadiene, bis-[2-(3′-tert-butyl-2′-hydroxy-5′-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4hydroxybenzyl-mercaptoacetic acid-isooctylester, bis-(4-tert-butyl-3-hydroxy-2,6-dimethyl-benzyl)dithiol-terephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols 4-Hydroxy-lauric acid anilide, 4-hydroxy-stearic acid anilide, 2,4-bis-octylmercapto-6-(3,5-di-tert-butyl-4hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, trishydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, trishydroxyethyl isocyanurate,thiodiethylene glycol, dihydroxyethyl-oxalic acid diamide.

9. Amides of β-(3,5-Di-tert-butyl-4-hydroxyphenyl)-propionic acid for example N,N′-Bis-(3,5-di-tert-butyl-4-hydroxyphenylpropionyl)-hexamethylene-diamine, N,N′-bis-(3,5-di-tert-butyl-4-hydroxy-phenylpropionyl)-trimethylene-diamine, N,N′-bis(3,5-di-tert-butyl-4-hydroxyphenylpropionyl)-hydrazine.

Examples of amine antioxidants: N,N′-Di-isopropyl-p-phenylenediamine, N,N′-di-sec.-butyl-p-phenylenediamine, N,N′-bis(1,4-dimethyl-pentyl)-p-phenylenediamine, N,N′-bis(1-ethyl-3-methyl-pentyl)-p-phenylenediamine, N,N′-bis(1-methyl-heptyl)-p-phenylenediamine, N,N′-dicyclohexyl-p-phenylenediamine, N,N′-diphenyl-p-phenylenediamine, N,N′-di-(naphthyl-2-)-p-phenylenediamine, N-isopropyl-N′-phenyl-p-phenylenediamine, N-(1-dimethylbutyl)-N′-phenyl-p-phenylenediamine, N-(1,3-methylheptyl)-N′-phenyl-p-phenylene-diamine, N-cyclohexyl-N′-phenyl-p-phenylenediamine, 4-(p-toluene-sulfonamido)-diphenylamine, N,N′-dimethyl-N,N′-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p′-di-tert-octyldiphenylamine, 4-n-butylaminophenol, 4-butyrylamino-phenol, 4-nonanoylamino-phenol, 4-dodecanoyloamino-phenol, 4-octadecanoyl-amino-phenol, di-(4-methoxy-phenyl)-amine, 2,6-di-tert-butyl-4-dimethyl-amino-methyl-phenol, 2,4′-diamino-diphenylmethane, 4,4′-diaminodiphenyl-methane, N,N,N′,N′-tetramethyl-4,4′-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1 ′,3′-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allylphenothiazine, tert-octylated phenothiazine, 3,7-di-tert-octylphenothiazine.

Examples for other antioxidants:

Aliphatic or aromatic phosphites, esters of thiodipropionic acid or of thiodiacetic acid, or salts of dithiocarbamic or dithiophosphoric acid.

Examples of metal passivators, for example for copper, are:

Triazoles, benzotriazoles and derivatives thereof, tolutriazole and derivatives thereof, e.g. di(2-ethylhexyl)-aminomethyltolutriazole, 2-mercaptobenzothiazole, 5,5′-methylene-bis-benzotriazole, 4,5,6,7-tetrahydrobenzo-triazole, salicyclidene-propylene-diamine and salicyclamino-guanidine and salts thereof, 1,2,4-triazole and N,N′-disubstituted aminomethyl triazoles of formula

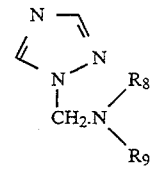

in which R8 and R9 are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g. I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula $$R_{12}-X_2-CH_2-CH(OH)-CH_2NR_{13}R_{14}$$

in which $X_2$ is —O—, —S—, —$SO_2$—C(O)—O— or —N(Rd) in which $R_{12}$ is H or $C_1$-$C_{12}$alkyl, $R_{13}$ is unsubstituted $C_1$-$C_4$alkyl or $C_2$-$C_5$alkyl substituted by one to three hydroxyl groups, $R_{14}$ is hydrogen, unsubstituted $C_1$-$C_4$alkyl or $C_2$-$C_5$alkyl substituted by one to three hydroxyl groups provided that at least one of $R_{13}$ and $R_{14}$ is hydroxy-substituted, and $R_{12}$ is $C_2$-$C_{20}$alkyl —$CH_2$—CH(OH)—$CH_2NR_{13}R_{14}$ or $R_{12}$ is $C_2$-$C_{18}$alkenyl, $C_2$-$C_3$alkynyl or $C_5$-$C_{12}$cycloalkyl provided that, when $X_2$ is —O— or —C(O)—O—, $R_{12}$ is branched $C_4$-$C_{20}$alkyl. These compounds are described in GB Patent Specification 2172284A.

h) Compounds having the formula:

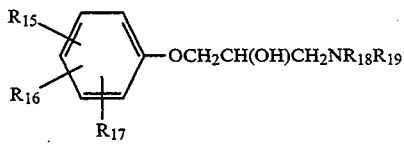

in which $R_{15}$, $R_{16}$, $R_{17}$ are, independently, hydrogen, $C_1$-$C_{15}$alkyl, $C_5$-$C_{12}$cycloalkyl, $C_6$-$C_{15}$aryl or $C_7$-$C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each —$CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are:

Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are:

Polymethacrylates, alkylated naphthalene derivatives.

Examples of dispersants/detergents are:

Polybutenylsuccinic acid-amides or -imides, polybutenyl-phosphonic acid derivatives, basic magnesium-, calcium-, and bariumsulfonates and -phenolates.

Examples of anti-wear additives and extreme pressure additives are:

Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The following examples are presented for the purpose of illustration only and are not to be construed to limit the scope or nature of the instant invention in any manner whatsoever.

EXAMPLE 1

2,4,8,10-Tetra-tert-butyl-6-(1,2:5,6-di-O-isopropylidene-D-glucofuranosyloxy)dibenzo[d,f][1,3,2]dioxaphosphepin To a solution of 4.1 g (30 mmol) of phosphorus trichloride in 100 ml of toluene cooled with an ice bath is added dropwise a solution of 13.2 g (30 mmol) of 3,3',5,5'-tetra-tert-butyl-2,2'-dihydroxydiphenyl and 6.1 g (60 mmol) of triethylamine in 50 ml of toluene. The reaction mixture is stirred at room temperature overnight. The mixture is then cooled with an ice bath and a solution of 7.8 g (30 mmol) of 1,2:5,6-diisopropylidene-D-glucose (diacetone-D-glucose) and 3.04 g (30 mmol) of triethylamine in 60 ml of toluene (warmed to effect solution) is added. The reaction mixture is stirred at room temperature for 48 hours and the resultant suspension of triethylamine hydrochloride is removed by filtration. The solvent is removed under reduced pressure and the residue is recrystallized from a 9:1 mixture of acetonitrile:toluene to give 15.0 g (71% yield) of a white crystalline solid which is a 92:8 (major:minor) mixture of diastereoisomers (by integration of peak areas in the $^{31}$PNMR spectrum) and melts at 170° C. Analysis: Calcd for $C_{40}H_{59}O_8P$: C, 68.7; H, 8.5. Found: C, 68.6; H, 8.5.

EXAMPLE 2

2,4,8,10-Tetra-tert-butyl-6-(1,2:3,4-di-O-isopropylidene-D-galactopyranosyloxy)dibenzo[d,f][1,3,2]-dioxaphosphepin When in the procedure of Example 1 an equivalent amount of 1,2:3,4-di-O-isopropylidene-D-galactopyranose is substituted for diacetone-D-glucose, the title compound is obtained, after recrystallization from methanol, in a yield of 75% as a white solid melting at 197°–200° C. Analysis: Calcd for $C_{40}H_{59}O_8P$: C, 68.7; H, 8.5. Found: C, 69.1; H, 8.7.

EXAMPLE 3

2,4,8,10-Tetra-tert-butyl-6-(1,2:4,5-di-O-isopropylidene-D-fructopyranosyloxy)-dibenzo[d,f][1,3,2]dioxaphosphepin The title compound is prepared when using the procedure of Example 1 a stoichiometrically equivalent amount of 1,2:4,5-di-O-isopropylidene-D-fructopyranose is used in place of 1,2:5,6-di-O-isopropylidene-D-glucose.

EXAMPLE 4

2,4,8,10-Tetra-tert-butyl-6-(2,3,4,6-tetra-O-benzyl-D-glucopyranosyloxy)dibenzo[d,f][1,3,2]dioxaphosphepin The title compound is prepared when using the procedure of Example 1 a stoichiometrically equivalent amount of 2,3,4,6-tetra-O-benzyl-D-glucopyranose is used in place of 1,2:5,6-di-O-isopropylidene-D-glucose.

EXAMPLE 5

2,4,8,10-Tetra-tert-butyl-6-(2,3,4,6-tetra-O-methyl-D-glucopyranosyloxy)dibenzo[d,f][1,3,2]dioxaphosphepin The title compound is prepared when using the procedure of Example 1 a stoichiometrically equivalent amount of 2,3,4,6-tetra-O-methyl-D-glucopyranose is used in place of 1,2:5,6-di-O-isopropylidene-D-glucose.

EXAMPLE 6

2,4,8,10-Tetra-tert-butyl-6-(2,3,6,2',3',4',6'-hepta-O-acetyl-D-cellobiosyloxy)dibenzo[d,f][1,3,2]dioxaphosphepin The title compound is prepared when using the procedure of Example 1 a stoichiometrically equivalent amount of 2,3,6-2',3',4',6'-hepta-O-acetyl-D-cellobiose (as prepared in U.S. Pat. No. 4,764,605) is used in place of 1,2:5,6-di-O-isopropylidene-D-glucose.

EXAMPLE 7

Process Stabilization of Propylene at 525° F. (274° C.)

This example illustrates the process stabilizing effectiveness of the instant compounds in old technology polypropylene.

The base formuation comprises unstabilized polypropylene (PROFAX 6501, Himont) containing 0.075% by weight of calcium stearate. The test additives are incorporated into the polyproyplene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder at 525° F. (274° C.) with a residence time of 90 seconds.

After each of the fast, third and fifth extrusions, the melt flow rate (in grams/10 minutes) is determined by ASTM method D1238 on the pellets obtained from the extruder. The results are given in the table below.

| Additive* | Concentration | Melt Flow after Extrusion | | |
|---|---|---|---|---|
| Compound of | (% by weight) | 1 | 3 | 5 |
| None | — | 9.0 | 25.1 | 66.6 |
| Example 1 | 0.05 | 6.2 | 11.3 | 24.4 |
| Example 2 | 0.05 | 4.9 | 7.8 | 13.6 |
| AO A | 0.05 | 8.1 | 11.1 | 17.5 |
| AO A plus Example 1 | 0.05 0.05 | 3.5 | 4.7 | 5.1 |
| AO A plus Example 2 | 0.05 0.05 | 3.9 | 4.7 | 5.0 |

*AO A is neopentanetetrayl tetrakis(3,5-di-tert-butyl-4-hydroxyhydrocinnamate).

The instant compounds are particularly effective in stabilizing polypropylene against thermal and oxidative degradation as shown by a minimum change in the melt flow rate both alone and in the presence of a representative phenolic antioxidant.

EXAMPLE 8

Long Term Heat Aging Stability of Polypropylene

Pellets obtained after the first extrusion in Example 7 are compression molded into 125 mil (3.2 mm) plaques at 450° F. (232° C.) and then oven aged at 150° C. in a forced draft oven equipped with a rotating carousel. The time, in days, to reach a yellowness index (YI) color change of 70 units is deemed to represent failure. Specimen yellowness index (YI) values are determined according to ASTM method D1925. Lower YI values indicate less discoloration.

The results are given in the table below.

| Additive* Compound of | Concentration (% by weight) | Days to Failure |
|---|---|---|
| AO A | 0.05 | 17 |
| AO A plus Example 1 | 0.05 0.05 | 47 |
| AO A plus Example 2 | 0.05 0.05 | 30 |

*AO A is neopentanetetrayl tetrakis(3,5-di-tert-butyl-4-hydroxyhydrocinnamate).

The instant compounds in combination with a representative phenolic antioxidant provide far superior long term heat aging stability to polypropylene than does the phenolic antioxidant alone.

EXAMPLE 9

Long Term Heat Aging Stability of Polypropylene

Pellets obtained after the first extrusion in Example 7 are compression molded into 40 mil (1.02 mm) plaques at 450° F. (232° C.) and then oven aged at 150° C. in a forced draft oven equipped with a rotating carousel. The time, in days, at which the 40 mil plaque will no longer bend over a 90° mandrel without cracking or showing signs of physical disintegration is deemed to represent failure. The results are given in the table below.

| Additive* Compound of | Concentration (% by weight) | Days to Failure |
|---|---|---|
| AO A | 0.05 | 8 |
| AO A plus Example 1 | 0.05 0.05 | 40 |
| AO A plus Example 2 | 0.05 0.05 | 14 |

*AO A is neopentanetetrayl tetrakis(3,5-di-tert-butyl-4-hydroxyhydrocinnamate).

The instant compounds in combination with a representative phenolic antioxidant provide far superior long term heat aging stability to polypropylene than does the phenolic antioxidant alone, particularly the instant compound of Example 1.

What is claimed is:

1. A stabilized composition which comprises
    (a) an organic material subject to oxidative or thermal degradation, and
    (b) an effective stabilizing amount of a compound of formula I

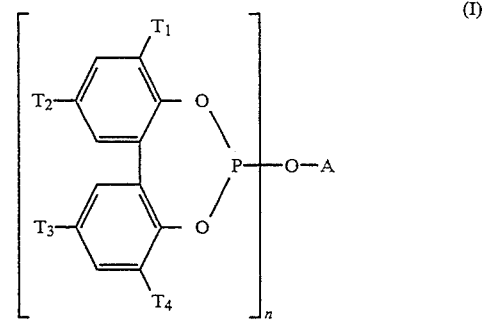

wherein
  n is 1 to 6,
  $T_1$, $T_2$, $T_3$ and $T_4$ are independently alkyl of 1 to 12 carbon atoms, cycloalkyl of 5 to 12 carbon atoms, aryl of 6 to 10 carbon atoms or phenylalkyl of 7 to 15 carbon atoms, and
  A is a carbohydrate residue.

2. A composition according to claim 1 where in the compound of formula I, A is of formula II or III

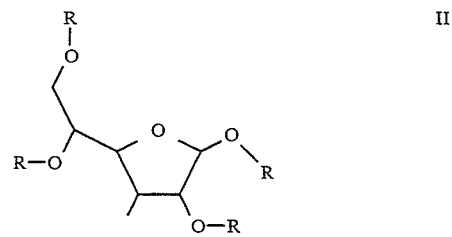

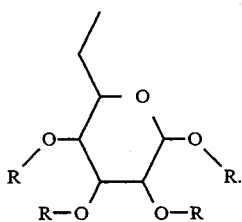

where R is a suitable protecting group which is benzyl or acetyl, or two vicinal R groups are isopropylidene.

3. A composition according to claim 1 wherein the organic material of component (a) is a organic polymer.

4. A composition according to claim 3 wherein the organic polymer is a polyolefin or a polyamide.

5. A composition according to claim 4 wherein the polyolefin is polypropylene.

6. A composition according to claim 2 wherein two vicinal R groups are ispropylidene.

7. A composition according to claim 1 where in the compound of formula I, n is 1 to 3, $T_1$ and $T_4$ are independently alkyl of 3 to 8 carbon atoms or phenylalkyl of 7 to 9 carbon atoms, and $T_2$ and $T_3$ are independently alkyl of 1 to 8 carbon atoms, cyclohexyl, phenyl or phenylalkyl of 7 to 9 carbon atoms.

8. A composition according to claim 7 wherein n is 1, $T_1$ to $T_4$ are independently alkyl of 4 to 8 carbon atoms.

9. A composition according to claim 8 wherein each of $T_1$ to $T_4$ is tert-butyl.

10. A composition according to claim 1 wherein the compound of formula I is
   2,4,8,10-tetra-tert-butyl-6-(1,2:5,6-di-O-isopropylidene-D-glucofuranosyloxy)-dibenzo[d,f][1,3,2]dioxaphosphepin;
   2,4,8,10-tetra-tert-butyl-6-(1,2:3,4-di-O-isopropylidene-D-galactopyranosyloxy)-dibenzo[d,f][1,3,2]-dioxaphosphepin;
   2,4,8,10-tetra-tert-butyl-6-(1,2:4,5-di-O-isopropylidene-D-fructopyranosyloxy)-dibenzo[d,f][1,3,2]dioxaphosphepin;
   2,4,8,10-tetra-tert-butyl-6-(2,3,4,6-tetra-O-benzyl-D-glucopyranosyloxy)-dibenzo[d,f][1,3,2]dioxaphosphepin;
   2,4,8,10-tetra-tert-butyl-6-(2,3,4,6-tetra-O-methyl-D-glucopyranosyloxy)-dibenzo[d,f][1,3,2]dioxaphosphepin; or
   2,4,8,10-tetra-tert-butyl-6-(2,3,6,2',3',4',6'-hepta-O-acetyl-D-cellobiosyloxy)-dibenzo[d,f][1,3,2]dioxaphosphepin.

11. A composition according to claim 1 wherein the compound of formula I is
   2,4,8,10-tetra-tert-butyl-6-(1,2:5,6-di-O-isopropylidene-D-glucofuranosyloxy)-dibenzo[d,f][1,3,2]dioxaphosphepin; or
   2,4,8,10-tetra-tert-butyl-6-(1,2:3,4-di-O-isopropylidene-D-galactopyranosyloxy)-dibenzo[d,f][1,3,2]-dioxaphosphepin.

* * * * *